(12) United States Patent
Tsai et al.

(10) Patent No.: US 11,426,181 B2
(45) Date of Patent: Aug. 30, 2022

(54) TOOL FOR BONE IMPLANT

(71) Applicant: METAL INDUSTRIES RESEARCH & DEVELOPMENT CENTRE, Kaohsiung (TW)

(72) Inventors: Tung-Lin Tsai, Tainan (TW); Chun-Chieh Tseng, Kaohsiung (TW); Yue-Jun Wang, New Taipei (TW); Chun-Ming Chen, Kaohsiung (TW); Li-Wen Weng, Kaohsiung (TW); Pei-Hua Wang, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 88 days.

(21) Appl. No.: 17/165,037

(22) Filed: Feb. 2, 2021

(65) Prior Publication Data
US 2022/0133336 A1 May 5, 2022

(30) Foreign Application Priority Data
Nov. 4, 2020 (TW) ................................. 109138444

(51) Int. Cl.
*A61B 17/16* (2006.01)
*A61B 17/00* (2006.01)

(52) U.S. Cl.
CPC ...... *A61B 17/1631* (2013.01); *A61B 17/1633* (2013.01); *A61B 2017/00561* (2013.01); *A61B 2017/00876* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633

See application file for complete search history.

(56) References Cited

U.S. PATENT DOCUMENTS

| | | | | |
|---|---|---|---|---|
| 2011/0319912 | A1* | 12/2011 | Nishio | A61B 34/20 606/130 |
| 2012/0152045 | A1* | 6/2012 | Isobe | B23B 39/14 74/22 R |
| 2014/0207141 | A1* | 7/2014 | Kehres | A61B 17/1778 606/80 |
| 2021/0100563 | A1* | 4/2021 | Sansoucy | A61B 17/1615 |
| 2021/0100564 | A1* | 4/2021 | Magno | A61B 17/32002 |
| 2022/0079655 | A1* | 3/2022 | Zucker | A61B 18/14 |
| 2022/0133336 | A1* | 5/2022 | Tsai | A61B 17/1631 606/80 |

* cited by examiner

*Primary Examiner* — Eric S Gibson
(74) *Attorney, Agent, or Firm* — Karin L. Williams; Alan D. Kamrath; Mayer & Williams PC

(57) ABSTRACT

A tool for a bone implant includes a sleeve and a transmission rod including a transmission member disposed on an end of a shaft. Another end of the shaft is located outside of the sleeve. The transmission member is received in the sleeve and includes a first compartment and a plurality of first teeth surrounding the first compartment. A drilling rod includes a second compartment and a plurality of second teeth surrounding the second compartment. A coupling portion is disposed between the second compartment and a bit. The coupling portion is coupled with the sleeve. The bit is located outside of the sleeve. Two magnets are disposed in the first and second compartments, respectively. Two same poles respectively of the two magnets face each other.

9 Claims, 4 Drawing Sheets

TOOL FOR BONE IMPLANT

CROSS REFERENCE TO RELATED APPLICATION

The application claims the benefit of Taiwan application serial No. 109138444, filed on Nov. 4, 2020, and the entire contents of which are incorporated herein by reference.

BACKGROUND OF THE INVENTION

1. Field of the Invention

The present invention relates to a tool for operation and, more particularly, to a tool for a bone implant for proceeding with a hole drilling operation in a bone surgery.

2. Description of the Related Art

If a proper treatment is not timely given when bone damage occurs, the blood circulation supplied to the bone would be destroyed or blocked, leading to osteonecrosis that causes collapse of bone, etc. General treatments for treating bone damage include implantation of a bone implant, such as a bone nail or a bone plate, which requires a hole drilling operation on a bone during the surgery.

Current drilling operation requires an operator to manually hold an electric drill to remove the bone tissues at a place to be drilled by a bit rotating at a high speed. During the hole drilling process, the operator has to continuously apply a force towards the drilling direction, and a much larger force must be applied when drilling a hole on a cortical bone that is harder. Namely, before the bit drills through the bone, the operator will apply a significantly large force. Thus, if the bit is not pulled backwards or stopped in time at the moment the bone is drilled through, the tip of the bit will damage the nearby soft tissue of the bone. Accordingly, current hole drilling process rely on the experience and the feel of hands of the operator to avoid excessively fast drilling speeds and excessively larger drilling forces that would result in sequela of damaged soft tissues, leading to medical disputes.

In view of the above, improvement to the current drilling tools for bone surgery is necessary. On the other hand, according to domestic and foreign papers and discussions on bone injury, one of the critical factors of post-surgery osteonecrosis is drilling the bone at a temperature higher than 47° C. during operation. Therefore, the temperature of the drilling tool during the drilling process is an important issue requiring high attention.

SUMMARY OF THE INVENTION

To solve the above-mentioned problems, it is an objective of the present invention to provide a tool for a bone implant, which tool will lose its drilling function at the moment drilling through the bone, avoiding damage to soft tissues.

It is another objective of the present invention to provide a tool for a bone implant, which tool has low friction between components thereof prolonging the service life of the components, avoiding annoying noise during operation, and making the temperature rise of the bone-drilling components difficult.

It is a further objective of the present invention to provide a tool for a bone implant to further assist in cooling of the components for drilling the bone, assuring the temperature of components for drilling the bone is lower than 47° C.

It is still another objective of the present invention to provide a tool for a bone implant to increase the stability during the hole drilling process and to reduce vibration, such that the size of the hole after drilling is more precise, improving the initial-stage stability after the implantation of the bone implant and reducing osteonecrosis.

As used herein, the term "a" or "an" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

As used herein, the term "coupling", "engagement", "assembly", or similar terms is used to include separation of connected members without destroying the members after connection or inseparable connection of the members after connection. A person having ordinary skill in the art would be able to select according to desired demands in the material or assembly of the members to be connected.

A tool for a bone implant according to the present invention includes a sleeve and a transmission rod including a shaft and a transmission member disposed on an end of the shaft. Another end of the shaft is located outside of the sleeve. The transmission member is received in the sleeve and includes a first compartment and a plurality of first teeth surrounding the first compartment. A drilling rod includes a second compartment and a plurality of second teeth surrounding the second compartment. A coupling portion is disposed between the second compartment and a bit. The coupling portion is coupled with the sleeve. The bit is located outside of the sleeve. Two magnets are disposed in the first compartment and the second compartment, respectively. Two same poles respectively of the two magnets face each other. When the bit abuts against a bone, the plurality of second teeth meshes with the plurality of first teeth, such that the drilling rod is driven by the transmission rod to rotate jointly for drilling the bone until the bone is drilled through. A repulsive force between the two magnets disengages the plurality of second teeth from the plurality of first teeth when the bone is drilled through.

Thus, the tool for the bone implant according to the present invention utilizes the transmission rod and the drilling rod meshed with the transmission rod as well as cooperating with the two magnets to permit joint rotation of the transmission rod and the drilling rod during the hole drilling process on the bone and to permit the transmission rod to disengage from the drilling rod at the moment the bone is drilled through, disabling the drilling function of the drilling rod to effectively avoid damage to the soft tissue by the drilling rod. Furthermore, the tool for the bone implant has a simple structure and can reduce the noise, vibration, and temperature rise during operation, improving the stability and efficiency during the hole drilling process. Thus, an operator can rapidly position and drill holes during the drilling process, improving the operational efficiency, improving the initial-stage stability of the bone implant after operation, and reducing osteonecrosis.

In an example, the tool for the bone implant further includes at least one stabilizing member disposed in the sleeve. The shaft of the transmission rod extends through the at least one stabilizing member. An outer periphery of the at least one stabilizing member is closer to an inner periphery of the sleeve than a portion of the transmission rod with a maximum width in the sleeve. Thus, the at least one stabilizing member and the sleeve together assist in reduction of wobbling of the transmission rod rotating at a high speed, thereby stabilizing the rotation to increase the hole drilling stability and to reduce vibration. Thus, the hole formed by drilling is more precise, increasing the initial-stage stability of the bone implant after operation and reducing osteonecrosis.

In an example, the at least one stabilizing member includes an inner race, an outer race, and a plurality of rolling members between the inner race and the outer race. The outer race is coupled to the inner periphery of the sleeve by loose fitting. Thus, the friction between the at least one stabilizing member and the sleeve is reduced to achieve a better stabilizing effect without adversely affecting smoothness of axial displacement of the sleeve relative to the at least one stabilizing member, prolonging the service life of the components, reducing the operational noise, and making the temperature rise of the drilling rod difficult.

In an example, the outer race does not contact with any component received in the sleeve except for the plurality of rolling members. This can effectively avoid frictional damage and generation of heat resulting from the difference in the rotational speeds of the outer race and other components, reducing the operational noise and vibration and making the temperature rise of the drilling rod difficult.

In an example, the tool for the bone implant further includes a limiting ring coupled to the shaft of the transmission rod. The transmission rod includes an abutting shoulder received in the sleeve. The at least one stabilizing member is disposed between the limiting ring and the abutting shoulder. Thus, the at least one stabilizing member can be restricted between the limiting ring and the abutting shoulder without axial displacement relative to the shaft, increasing assembling convenience and reducing operational vibration.

In an example, the plurality of second teeth meshes with the plurality of first teeth by linear contact. Thus, the plurality of first teeth can be disengaged from the plurality of second teeth more easily, reducing wear of the components and improving operational smoothness.

In an example, each of the plurality of first teeth and the plurality of second teeth has gradually reducing widths from a bottom thereof towards a free end thereof. Thus, the plurality of second teeth can mesh with the plurality of first teeth more easily, reducing wear of the components and improving operational smoothness.

In an example, the tool for the bone implant further includes a cooling member including a jacket having an inner periphery abutting an outer periphery of the sleeve. The cooling member further includes a heat pipe disposed between the inner periphery of the jacket and an outer periphery of the jacket, and the heat pipe provides a vacuum environment and is filled with a phase-changing fluid. Thus, the heat pipe can absorb the heat energy of the jacket, and the phase-changing fluid can proceed with liquid-gas phase transition to carry the heat energy away, assisting in the cooling effect.

In an example, the heat pipe includes two helical tubes intercommunicating with each other to improve the cooling efficiency.

BRIEF DESCRIPTION OF THE DRAWINGS

The present invention will become clearer in light of the following detailed description of illustrative embodiments of this invention described in connection with the drawings.

Figure 1:
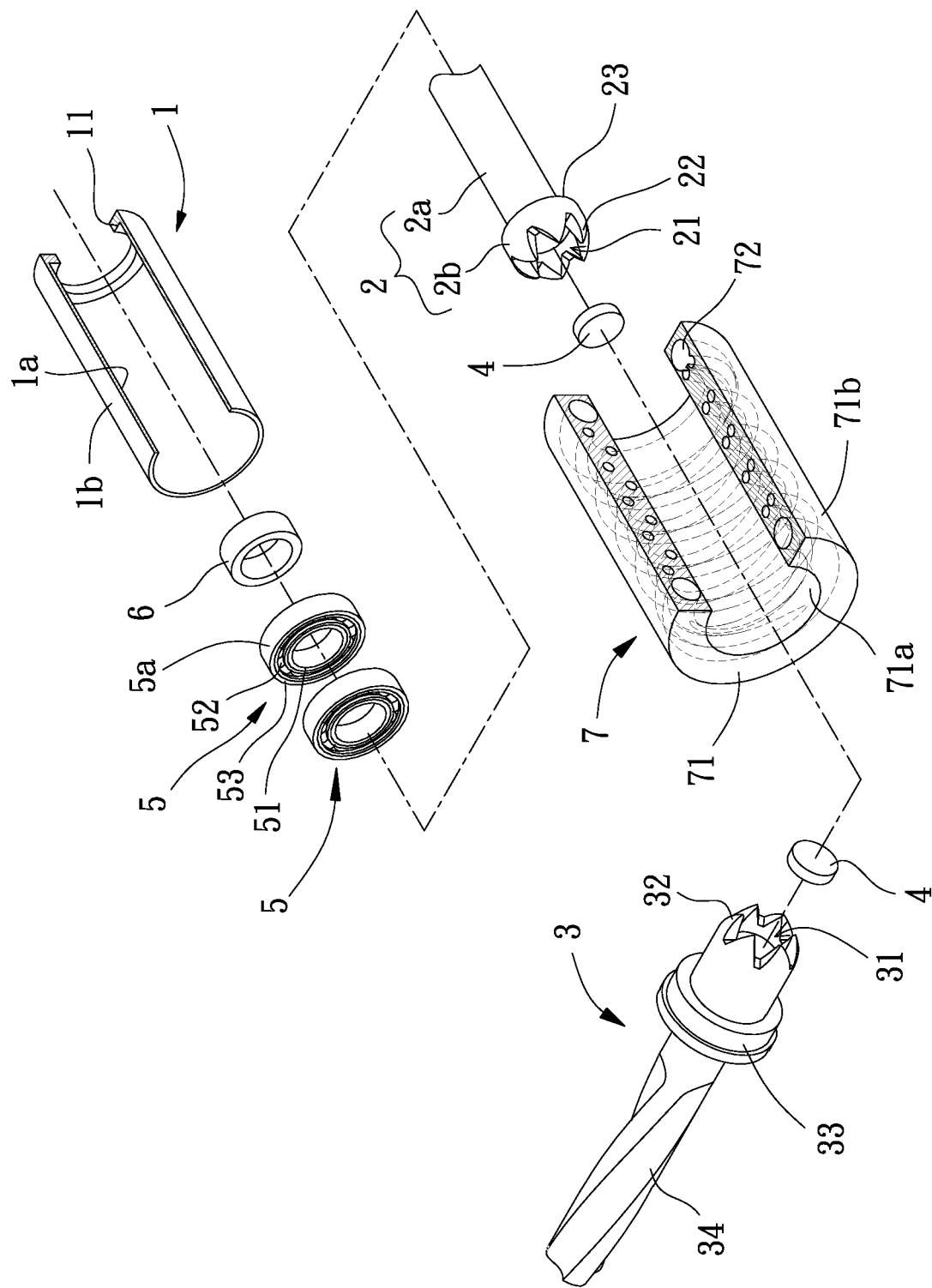
FIG. 1 is an exploded, perspective view of a tool for a bone implant of an embodiment according to the present invention.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

DETAILED DESCRIPTION OF THE INVENTION

Figure 2:
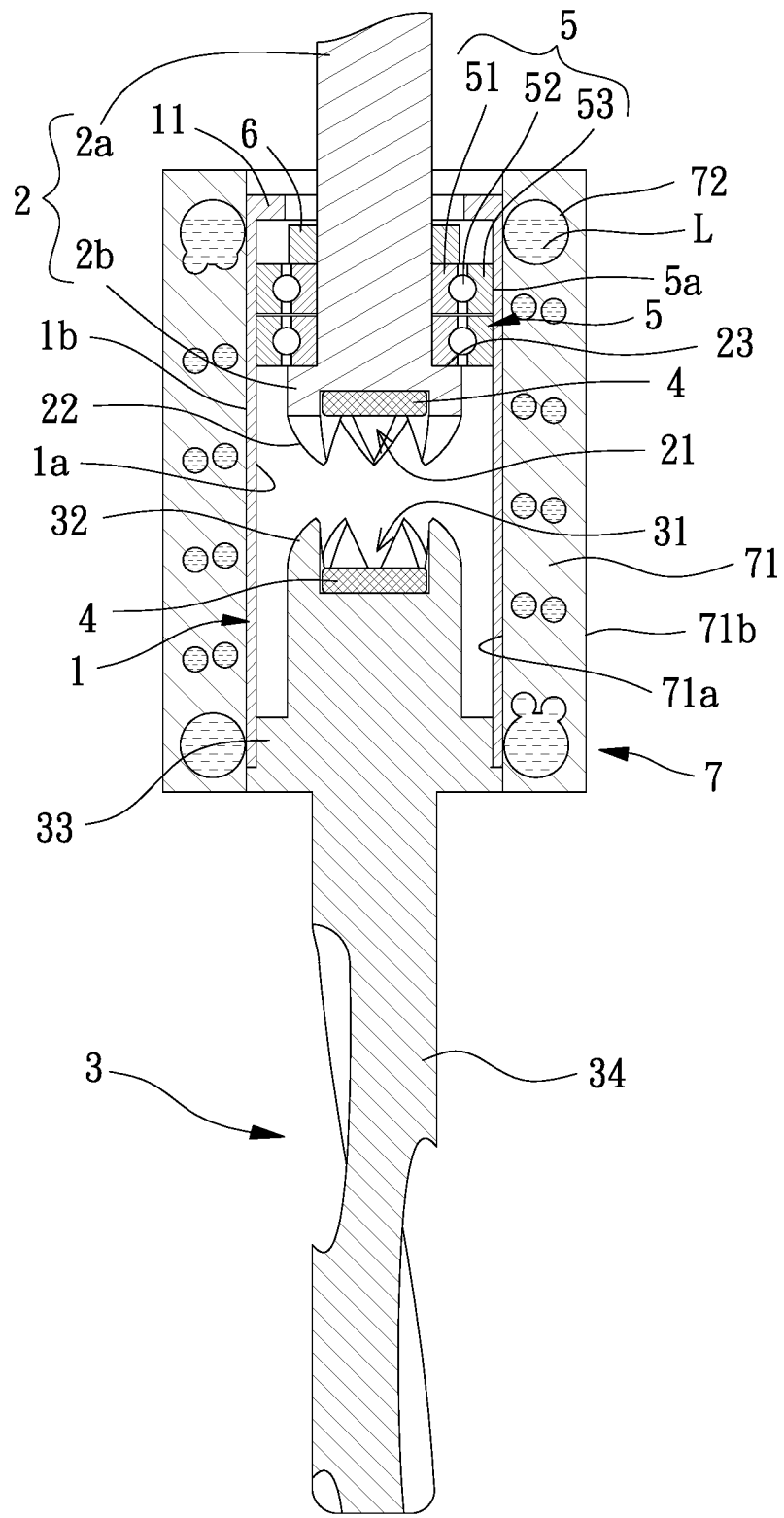
FIG. 2 is a cross sectional view of the tool of FIG. 1 after assembly.

With reference to FIGS. 1 and 2, a tool for a bone implant of an embodiment according to the present invention includes a sleeve 1, a transmission rod 2, a drilling rod 3, and two magnets 4. An end of the transmission rod 2, an end of the drilling rod 3, and the two magnets 4 are received in the sleeve 1.

Two ends of the sleeve 1 are open. Furthermore, the sleeve 1 includes an inner periphery 1a and an outer periphery 1b opposite to the inner periphery 1a. One of the two ends of the sleeve 1 can have an inner flange 11 to avoid components received in the sleeve 1 from falling out.

Figure 3:
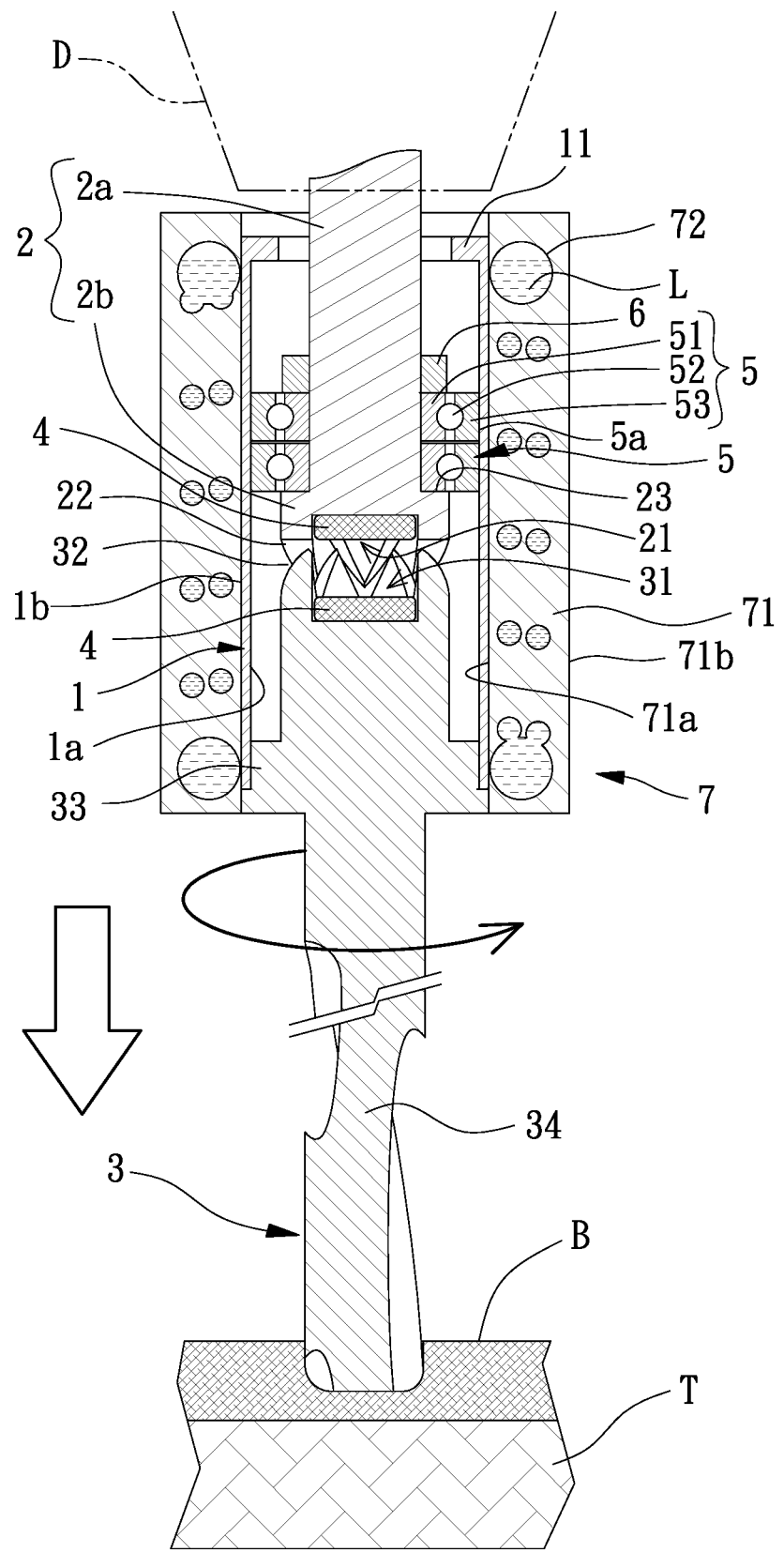
FIG. 3 is a cross sectional view illustrating use of the tool of the embodiment according to the present invention for drilling a bone.

The transmission rod 2 includes a shaft 2a and a transmission member 2b disposed on an end of the shaft 2a. The transmission member 2b is received in the sleeve 1 for coupling with the drilling rod 3. Another end of the shaft 2a is located outside of the sleeve 1 for coupling with a drilling machine D (only a part of the drilling machine D is shown in FIG. 3). The transmission member 2b can be coupled with the shaft 2a or integrally formed with the shaft 2a. The present invention is not limited in this regard.

The transmission member 2b includes a first compartment 21 and a plurality of first teeth 22. The first compartment 21 receives one of the two magnets 4. The plurality of first teeth 22 may surround the first compartment 21. In this embodiment, the plurality of first teeth 22 is arranged annularly about an axis of the shaft 2a. Each of the plurality of first teeth 22 has gradually reducing widths from a bottom thereof towards a free end thereof presenting a shape like a triangular tooth. Preferably, the free end of each of the plurality of first teeth 22 is rounded, such that each of the plurality of first teeth 22 is arcuate from an outer face of the free end towards an inner face of the free end. Furthermore, two sides of the free end of each of the plurality of first teeth 22 are slanted to make the inner face smaller than the outer face. The transmission rod 2 can further include an abutting shoulder 23 received in the sleeve 1 to provide abutting and positioning for other components. The form of the abutting shoulder 23 is not limited in the present invention. As an example, a flange can be formed on an outer periphery of the shaft 2a. In an alternative example shown in the figures of this embodiment, the diameter of the transmission member 2b is larger than the diameter of the shaft 2a, such that an intersection between the transmission member 2b and the shaft 2a forms the abutting shoulder 23

The drilling rod 3 includes a second compartment 31 for receiving the other magnet 4. The drilling rod 3 further includes a plurality of second teeth 32 for meshing with the plurality of first teeth 22. The plurality of second teeth 32 can surround the second compartment 31. In this embodiment, the drilling rod 3 can be coaxial with the shaft 2a of the transmission rod 2. The plurality of second teeth 32 may be arranged annularly about an axis of the drilling rod 3. Each of the plurality of second teeth 32 has gradually reducing widths from a bottom thereof towards a free end thereof, presenting a shape like a triangular tooth. Preferably, the free end of each of the plurality of second teeth 32 is rounded. Thus, the plurality of second teeth 32 can mesh with the plurality of first teeth 22 by linear contact, which can be disengaged from each other more easily than the surface contact.

The drilling rod 3 can further include a coupling portion 33 disposed between the second compartment 31 and a bit 34, such that the drilling rod 3 can couple with the sleeve 1 by the coupling portion 33, assuring joint rotation of the sleeve 1 and the drilling rod 3. Furthermore, after the coupling portion 33 is coupled with the sleeve 1, the second compartment 31 and the plurality of second teeth 32 are received in the sleeve 1, and the bit 34 is located outside of the sleeve 1 for drilling a bone.

The two magnets 4 are disposed in the first compartment 21 and the second compartment 31, respectively. Two same poles (such as the N poles or the S poles) respectively of the two magnets 4 face each other. Thus, a repulsive force is generated when the two magnets 4 are close to each other.

The tool for the bone implant can further comprise at least one stabilizing member 5 to assist in reducing wobbling of the transmission rod 2 rotating at a high speed, thereby stabilizing the rotation of the transmission rod 2. The at least one stabilizing member 5 can be disposed in the sleeve 1, and the shaft 2a of the transmission rod 2 extends through the at least one stabilizing member 5. An outer periphery 5a of the at least one stabilizing member 5 is closer to the inner periphery 1a of the sleeve 1 than a portion of the transmission rod 2 with the maximum width thereof in the sleeve 1. In this embodiment, the portion of the transmission rod 2 with the maximum width is at a location near the abutting shoulder 23 of the transmission member 2b. Thus, even if the shaft 2a of the transmission rod 2 is elongated, wobbling of the transmission member 2b of the transmission rod 2 can be reduced by at least one stabilizing member 5 together with the sleeve 1.

Furthermore, to further reduce the friction between the outer periphery 5a of the at least one stabilizing member 5 and the inner periphery 1a of the sleeve 1, the at least one stabilizing member 5 includes a plurality of rolling members 52 between an inner race 51 and an outer race 53. The inner race 51 is disposed around the outer periphery of the shaft 2a. The plurality of rolling members 52 can roll between the inner race 51 and the outer race 53 to achieve the above friction reduction effect. As an example, the at least one stabilizing member 5 can be a bearing in the form of a ball bearing, a needle roller bearing, or a tapered roller bearing. Although the figures of this embodiment show an example in the form of a ball bearing, the present invention should not be limited to this example. Furthermore, the outer race 53 can be coupled to the inner periphery 1a of the sleeve 1 by loose fitting to achieve a better stabilizing effect without adversely affecting smoothness in axial displacement of the sleeve 1 relative to the at least one stabilizing member 5.

Furthermore, this embodiment includes two stabilizing members 5 disposed coaxially to permit extension by the shaft 2a of the transmission rod 2, such that the axis of the shaft 2a is more difficult to wobble, enhancing the rotational stability of the transmission rod 2. In this non-restrictive embodiment, the two stabilizing members 5 are stacked, such that the inner races 51 of the two stabilizing members 5 abut each other, and the outer races 53 of the two stabilizing members 5 abut each other. Furthermore, the inner race 51 of one of the two stabilizing members 5 near the drilling rod 3 abuts against the abutting shoulder 23 of the transmission rod 2, and the outer race 53 of the one of the two stabilizing members 5 does not contact with the abutting shoulder 23. The inner race 51 of the other stabilizing member 5 distant to the drilling rod 3 is pressed by a limiting ring 6 coupled to the shaft 2a. The limiting ring 6 does not abut against the inner flange 11 of the sleeve 1. The outer race 53 of the other stabilizing member 5 does not contact with the limiting ring 6. Thus, the limiting ring 6 can be securely coupled to the transmission rod 2 to rotate jointly. Furthermore, the two stabilizing members 5 can be restricted between the limiting ring 6 and the abutting shoulder 23 without axial displacement relative to the shaft 2a. Furthermore, even if the limiting ring 6 does not work, the two stabilizing members 5 will be stopped by the inner flange 11 of the sleeve 1 and, thus, cannot disengage from the sleeve 1, improving the use safety.

The tool for the bone implant can further comprise a cooling member 7 including a jacket 71 having an inner periphery 71a abutting the outer periphery 1b of the sleeve 1 for absorbing heat energy transmitted to the sleeve 1. A heat pipe 72 is disposed between the inner periphery 71a and an outer periphery 71b of the jacket 71. The heat pipe 72 provides a vacuum environment and is filled with a phase-changing fluid L. Thus, the heat pipe 72 can absorb the heat energy of the jacket 71, and the phase-changing fluid L can proceed with liquid-gas phase transition to carry the heat energy away, assisting in the cooling effect. This assures that the temperature can be lower than 47° C. during drilling of the bone, lowering the risk of osteonecrosis. The form of the heat pipe 72 is not limited in the present invention. In this embodiment, the heat pipe 72 includes two helical tubes intercommunicating with each other to enhance the cooling effect.

With reference to FIG. 3, the tool for the bone implant according to the present invention can be applied to any hole drilling process in a bone implantation operation. In use, the shaft 2a of the transmission rod 2 is coupled to a drilling machine D, and the bit 34 of the drilling rod 3 abuts against a bone B. Under the reaction force acting on the bit 34 by the bone B, the drilling rod 3 is pushed towards the transmission rod 2 and overcomes the repulsive force between the two magnets 4 until the plurality of second teeth 32 meshes with the plurality of first teeth 22. Thus, when the drilling machine D drives the transmission rod 2 to rotate at a high speed, the drilling rod 3 is driven by the transmission rod 2 to rotate jointly, and the bit 34 drills the bone B.

Figure 4:
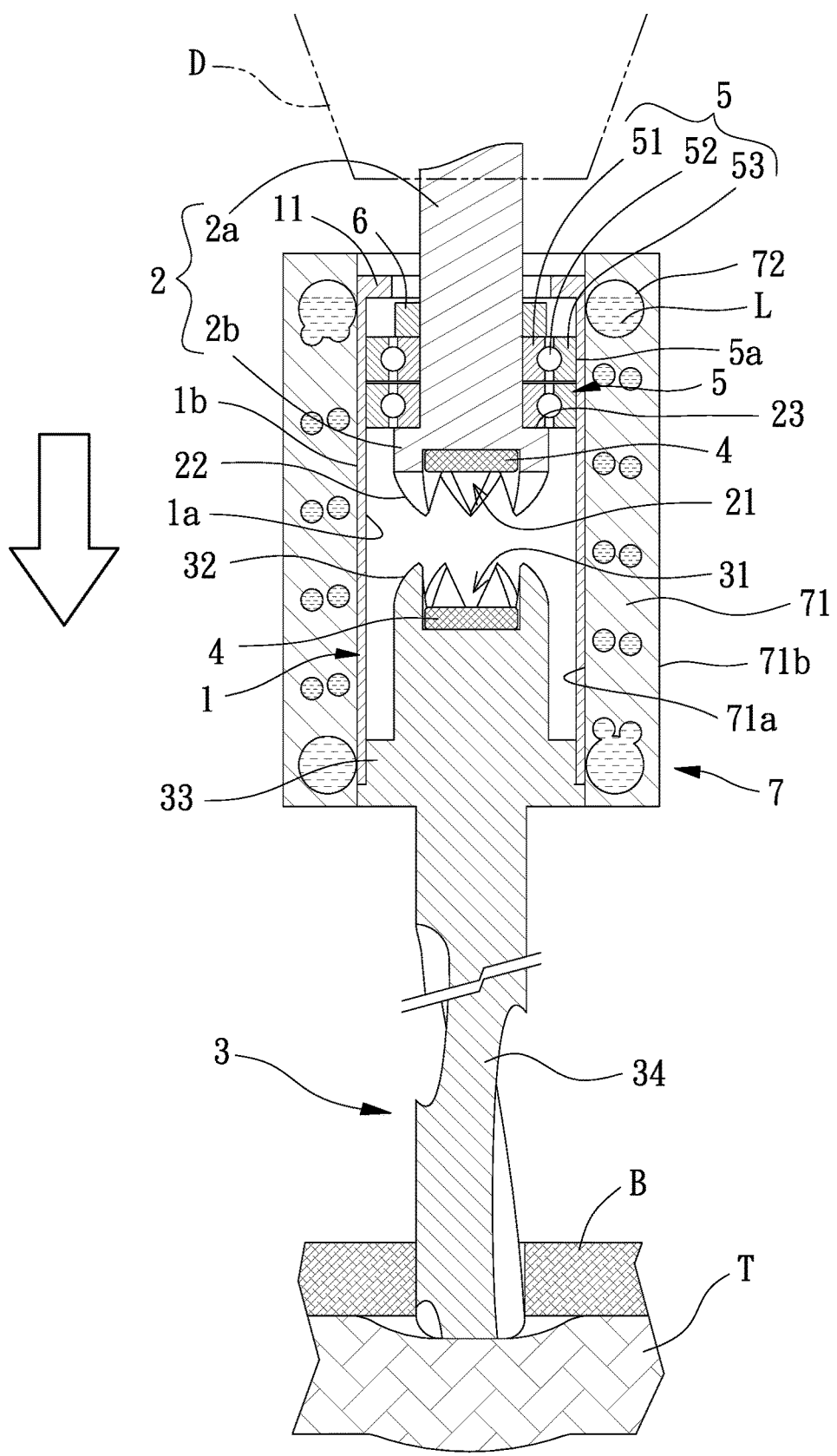
FIG. 4 is a cross sectional view illustrating drilling through the bone by the tool of the embodiment according to the present invention.

With reference to FIG. 4, the reaction force acting on the bit 34 reduces suddenly at the moment the bone B is drilled through, such that the plurality of first teeth 22 disengages from the plurality of second teeth 32 under the repulsive force between the two magnets 4, displacing the drilling rod 3 away from the transmission rod 2. Thus, the rotating transmission rod 2 cannot drive the drilling rod 3 which will stop rotating. This significantly avoids the soft tissue T on the surface of the bone B from being injured by the bit 34. Furthermore, the force applied through the drilling rod 3 towards the soft tissue T assists in peeling of the film between the soft tissue T and the bone B.

During the bone drilling process, the transmission rod 2 drives the drilling rod 3 to rotate, and the sleeve 1 coupled to the drilling rod 3 and the cooling member 7 coupled to the sleeve 1 are driven to rotate synchronously. The outer races 53 of the stabilizing members 5 could contact with the inner periphery 1a of the sleeve 1 due to wobbling of the transmission rod 2 while the drilling rod 3 is subject to force, such that the outer races 53 could be driven by the sleeve 1 to rotate jointly. Thus, the outer races 53 of the stabilizing members 5 will not rotate continuously and synchronously with the sleeve 1. Nevertheless, in the tool for a bone implant of this embodiment, the outer races 53 do not contact with any components received in the sleeve 1 except for the plurality of rolling members 52, which can effectively avoid frictional damage and generation of heat resulting from the difference between the rotational speeds of the outer races 53 and other components. At the same time, the two magnets 4 disengage the transmission rod 2 from the drilling rod 3 by force at a distance without contact. Therefore, the friction between the components in the sleeve 1 can be further reduced or even becomes zero. This not only prolongs the service life of the components but also significantly reduces the operational noise and vibration. Furthermore, the temperature of the drilling rod 3 is less likely to increase, reducing the risk of osteonecrosis and shortening the waiting time (which requires lowering the temperature of drilling rod 3) between two hole drilling processes. This is helpful in shortening the operation time and the operational risks.

It is noted that vibration or wobbling of the drilling rod 3 will cause the formed hole to be larger than the expected size, such that the bone implant cannot be securely implanted or the stability at initial stage after implantation is poor. According to studies, when a gap larger than 100 μm exists between the bone implant and an inner periphery of the hole, the bone cannot securely couple with the bone implant after healing. Thus, the tool for a bone implant according to the present invention can reduce the operational vibration, such that the hole drilled by the drilling rod 3 is more precise, which is greatly helpful in the initial-stage stability and the long-term stability after implantation.

In view of the foregoing, the tool for the bone implant according to the present invention utilizes the transmission rod and the drilling rod meshed with the transmission rod as well as cooperating with the two magnets to permit joint rotation of the transmission rod and the drilling rod during the hole drilling process on the bone and to permit the transmission rod to disengage from the drilling rod at the moment the bone is drilled through, disabling the drilling function of the drilling rod to effectively avoid damage to the soft tissue by the drilling rod. Furthermore, the tool for the bone implant has a simple structure and can reduce the noise, vibration, and temperature rise during operation, improving the stability and efficiency during the hole drilling process. Thus, an operator can rapidly position and drill holes during the drilling process, improving the operational efficiency, improving the initial-stage stability of the bone implant after operation, and reducing osteonecrosis.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A tool for a bone implant, comprising:
   a sleeve;
   a transmission rod including a shaft and a transmission member disposed on an end of the shaft, wherein another end of the shaft is located outside of the sleeve, wherein the transmission member is received in the sleeve and includes a first compartment and a plurality of first teeth surrounding the first compartment;
   a drilling rod including a second compartment and a plurality of second teeth surrounding the second compartment, wherein a coupling portion is disposed between the second compartment and a bit, wherein the coupling portion is coupled with the sleeve, and wherein the bit is located outside of the sleeve; and
   two magnets disposed in the first compartment and the second compartment, respectively, wherein two same poles respectively of the two magnets face each other, wherein when the bit abuts against a bone, the plurality of second teeth meshes with the plurality of first teeth, such that the drilling rod is driven by the transmission rod to rotate jointly for drilling the bone until the bone is drilled through, and wherein a repulsive force between the two magnets disengages the plurality of second teeth from the plurality of first teeth when the bone is drilled through.

2. The tool for the bone implant as claimed in claim 1, further comprising at least one stabilizing member disposed in the sleeve, wherein the shaft of the transmission rod extends through the at least one stabilizing member, wherein an outer periphery of the at least one stabilizing member is closer to an inner periphery of the sleeve than a portion of the transmission rod with a maximum width in the sleeve.

3. The tool for the bone implant as claimed in claim 2, wherein the at least one stabilizing member includes an inner race, an outer race, and a plurality of rolling members between the inner race and the outer race, and wherein the outer race is coupled to the inner periphery of the sleeve by loose fitting.

4. The tool for the bone implant as claimed in claim 3, wherein the outer race does not contact with any component received in the sleeve except for the plurality of rolling members.

5. The tool for the bone implant as claimed in claim 2, further comprising a limiting ring coupled to the shaft of the transmission rod, wherein the transmission rod includes an abutting shoulder received in the sleeve, and wherein the at least one stabilizing member is disposed between the limiting ring and the abutting shoulder.

6. The tool for the bone implant as claimed in claim 1, wherein the plurality of second teeth meshes with the plurality of first teeth by linear contact.

7. The tool for the bone implant as claimed in claim 1, wherein each of the plurality of first teeth and the plurality of second teeth has gradually reducing widths from a bottom thereof towards a free end thereof.

8. The tool for the bone implant as claimed in claim 1, further comprising a cooling member including a jacket having an inner periphery abutting an outer periphery of the sleeve, wherein the cooling member further includes a heat pipe disposed between the inner periphery of the jacket and an outer periphery of the jacket, and wherein the heat pipe provides a vacuum environment and is filled with a phase-changing fluid.

9. The tool for the bone implant as claimed in claim 8, wherein the heat pipe includes two helical tubes intercommunicating with each other.

* * * * *